United States Patent
Andreeff et al.

(10) Patent No.: US 7,204,996 B2
(45) Date of Patent: *Apr. 17, 2007

(54) METHOD OF CANCER TREATMENT

(75) Inventors: Michael Andreeff, Houston, TX (US); Elihu H Estey, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/150,461

(22) Filed: Jun. 10, 2005

(65) Prior Publication Data

US 2005/0238707 A1  Oct. 27, 2005

Related U.S. Application Data

(63) Continuation of application No. 10/419,025, filed on Apr. 18, 2003, now Pat. No. 6,929,802, which is a continuation of application No. 09/431,547, filed on Oct. 29, 1999, now abandoned.

(51) Int. Cl.
*A61K 9/127* (2006.01)

(52) U.S. Cl. .......................... 424/450; 514/25; 514/33; 514/34

(58) Field of Classification Search ................ 514/25, 514/33, 34; 424/450
See application file for complete search history.

(56) References Cited

U.S. PATENT DOCUMENTS 5,811,119 A * 9/1998 Mehta et al. ............... 424/450
5,821,254 A * 10/1998 Sporn et al. ................ 514/324
5,874,412 A * 2/1999 Priebe et al. ................. 514/34
5,902,604 A * 5/1999 Zou et al. .................... 424/450
6,929,802 B2 * 8/2005 Andreeff et al. ............ 424/450

OTHER PUBLICATIONS

Perez-Soler, Cancer Research, vol. 50, pp. 4260-4266, 1990.*
Zou, Cancer Research, vol. 54, pp. 1479-1484, 1984.*
Perez-Soler, Cnacer Chemother. Pharmacol. vol. 34, pp. 109-118, 1994.□□.*
Consoli, Blood, vol. 88, pp. 633-644, 1996□□Devita, Principles of Chemotherapy, ED., Philadelphia, 1993.*
Acton et al., "Intensely potent morpholinyl anthracyclines," *J. Med. Chem.*, 27:638-645, 1984.
Barbieri et al., "Chemical and biological characterization of 4'-iodo-4' deoxydoxorubicin," *Cancer Res.*, 47:4001-4006, 1987.
Chaudhary and Roninson, "Induction of multidrug resistance in human cells by transient exposure to difference chemotherapeutic drugs," *J. Natl. Cancer Inst.*, 85:632-639, 1993.
Consoli et al., The novel anthracycline annamycin is not affected by p-glycoprotein-related multidrug resistance: comparison with idarubicin and doxorubicin in HL-60 leukemia cells lines, *Blood*, 88(2):633-644, 1996.

(Continued)

*Primary Examiner*—Gollamudi S. Kishore
(74) *Attorney, Agent, or Firm*—Fulbright & Jaworski L.L.P.

(57) ABSTRACT

This invention comprises a method of treating a subject having relapsed or refractory cancer such as leukemia with liposomal annamycin including the steps of
 (a) evaluating the subject to determine if the subject has relapsed or refractory cancer;
 (b) administering a high-dose amount of liposomal-annamycin for at least 3 days in a 7 day period. First line cancer therapy with particular reference to leukemia is both contemplated and useful.

22 Claims, 1 Drawing Sheet

OTHER PUBLICATIONS

Dalton, "Overcoming the multidrug-resistant phenotype," *Principles and Practice of Oncology*, 4th Ed., 6:2655-2666, Philadelphia, 1993.

Den Boer et al., "Optimal immunocytochemical and flow cytometric detetection of P-gp, MRP and LRP in childhood acute lymphoblastic leukemia," *Leukemia*, 11:1078-1085, 1997.

DeVita et al., "Principles of chemotherapy", *Principles and Practice of Oncology*, 4th Ed., Philadephia, 1993.

Gabizon et al., "Liposomes as *in vivo* carriers of adriamycin: reduced cardiac uptake and preserved antitumor activity in mice," *Cancer Res.*, 42:4734-4739, 1982.

Ganapathi et al., "N-benzyladriamycin-14-valerate versus progressively doxorubicin-resistant murine tumors: cellular pharmacology and characterization of cross-resistance *in vitro* and *in vivo*," *Br. J. Cancer*, 60:819-826, 1989.

Hermann et al., "Prevention of chronic doxorubicin cardiotoxicity in beagles by liposomal encapsulation," *Cancer Res.*, 43:5427-5432, 1983.

Leith et al., "Correlation of multidrug resistance (MDRI) protein expression with functional dye/drug efflux in acute myeloid leukemia by multiparameter flow cytometry: identification of discordant MDR⁻/efflux⁺ and MDRI⁺/efflux⁻ cases," *Blood*, 86:2329-2343, 1995.

Marie, "Phenotypic and genotypic analyses of multidrug resistance (MDR) in clinical hospital practice," *Leukemia*, 11:1063-1066, 1997.

Mayhew et al., Inhibition of liver metastases of M 5076 tumor by liposome-entrapped adriamycin, *Cancer Drug Delivery*, 1:43-57, 1983.

Moscow and Cowan, "Multidrug resistance," *J. Natl. Cancer Inst.*, 80:14-20, 1989.

Perez-Soler and Priebe, "Anthracycline antibodies with high liposome entrapment; structural features and biological activity," *Cancer Res.*, 50:4260-4266, 1990.

Priebe et al., "Removal of the basic center from doxorubicin partially overcomes multidrug resistance and decreases cardiotoxicity," *Anticancer Drugs*, 4:37-48, 1993.

Rahman et al., Comparative pharmacokinetics of free doxorubicin and doxorubicin entrapped in cardiolipin liposomes, *Cancer Res.*, 46:2295-2299, 1986.

Zou et al., Antitumor activity of free and liposome-entrapped annamycin, a lipophilic anthracycline antibiotic with non-cross-resistance properties, ABSTRACT, *Cancer Res.*, 54:1479-1484, 1994.

Zou et al., "Organ distribution and tumor uptake of annamycin, a new anthracycline derivative with high affinity for lipid membranes, entrapped in multilamellar vesicles," *Cancer Chemother. Pharmacol.*, 32:190-196, 1993.

Zou et al., "Quantitative analysis of the lipophilic doxorubicin analog annamycin in plasma and tissue samples by reverse-phase chromatography," *J. Pharm Sciences*, 82:1151-1154, 1993.

* cited by examiner

METHOD OF CANCER TREATMENT

This application is a continuation of U.S. patent application Ser. No. 10/419,025, filed on Apr. 18, 2003 now U.S. Pat. No. 6,929,802, which is a continuation of U.S. patent application Ser. No. 09/431,547, filed on Oct. 29, 1999, now abandoned, the entire contents of each of which are incorporated herein by reference in their entirety.

FIELD OF THE INVENTION

This invention comprises a method of treating a subject having relapsed or refractory cancer such as leukemia with liposomal annamycin including the steps of
(a) evaluating the subject to determine if the subject has relapsed or refractory cancer;
(b) administering a high-dose amount of liposomal-annamycin for at least 3 days in a 7 day period. First line cancer therapy with particular reference to leukemia is both contemplated and useful.

BACKGROUND OF THE INVENTION

Doxorubicin is one of the most effective antitumor agents against hematological malignancies and certain human solid tumors such as breast carcinoma and osteosarcoma. However, its use is limited by acute myelosuppression, chronic cardiotoxicity, and natural or acquired drug resistance. In the last few years, there have been important advances in understanding the mechanisms of acquired resistance to doxorubicin and other structurally unrelated antitumor agents. Without being bound by any particular theory, it is now widely accepted that the overexpression of a membrane glycoprotein, P-glycoprotein, that acts as a drug efflux pump, mediates acquired resistance to doxorubicin in some in vitro systems and in vivo animal tumor models. It is also believed that overexpression of P-glycoprotein occurs in a significant number of cancer subjects when their tumors progress or relapse after treatment with doxorubicin. Despite the fact that 80% to 90% of patients with acute myeloid leukemia (AML) or acute lymphoid leukemia (ALL) achieve a complete remission following intensive induction chemotherapy, more than 50% of patients relapse, often because recurrence of disease is associated with clinical drug resistance.

Since the introduction of doxorubicin in the current anticancer armamentarium, extensive efforts have been devoted to the synthesis of analogs with improved properties. Initially, most efforts were directed towards the preparation of analogs with reduced cardiotoxic potential. Those efforts have only been partially successful. More recently, and triggered by the discovery of the phenomenon of multidrug resistance and the identification of P-glycoprotein, the synthetic efforts have been more focused towards obtaining analogs with non-cross-resistance properties. Several non-cross resistant analogs have been identified. They all have in common a markedly increased lipophilicity. Some of them have a similar mechanism of cytotoxicity to that of doxorubicin i.e., topoisomerase II inhibition. Others have a different mechanism of action, i.e., DNA alkylation Liposomes have been used extensively as carriers of doxorubicin and daunorubicin. Liposomal-doxorubicin was reported as less cardiotoxic and more active than doxorubicin in models of liver metastasis in mice by several investigators. Several clinical studies have been conducted with different liposomal formulations of doxorubicin. These trials have shown an MTD similar to that of free doxorubicin, a significant reduction of certain toxicities, such as gastrointestinal and vesicant effects, and an unchanged dose-limiting toxicity, i.e., myelosuppression.

Surprisingly, Annamycin is an anthracycline antibiotic that has now been found to display a lack of cross-resistance properties and a very high affinity for lipid membranes. Annamycin is completely insoluble in water solutions. Liposomal Annamycin is useful as a carrier for intravenous annamycin administration. Some researchers in the field believe that a fundamental mechanism of action of Annamycin is inhibition of topoisomerase-II. L-Annamycin has shown lack of cross-resistance in vivo in KB/-VI human xenografts and enhanced antitumor activity compared with doxorubicin in several mouse tumor models in vivo. In mice, the dose-limiting toxicity of L-Annamycin is myelosuppression and its cardiotoxic potential less than that of doxorubicin. In dogs, the dose equivalent to the mouse LD10 was very-well tolerated with no side effects, no blood chemical changes, and no pathological changes four weeks after drug administration.

The in vivo antitumor activity of L-Annamycin was tested in leukemia(L120), melanoma (B16), reticulosarcoma (m5076), and Lewis lung carcinoma cells.

Results in KB and KB-V1 human xenografts demonstrate that L-Annamycin was at least as effective as doxorubicin, with the greatest antitumor activity against L1210 leukemia cells. It has been demonstrated that Annamycin is cytotoxic in MDR overexpressing HL-60 cells and that its resistance index is lower than that of idarubicin and doxorubicin.

The resistance index of Annamycin was found to be lower than that of idarubicin and doxorubicin. Coincubation in the presence of verapamil resulted in 4.5 fold and 2 fold resistance index decreases of doxorubicin and idarubicin, respectively, whereas Annamycin did not change. This suggests Annamycin's ability to circumvent p-gp mediated MDR. Unlike doxorubicin and idarubicin, Annamycin is not affected by p-gp mediated MDR.

The in vitro cytotoxicity of L-Annamycin was tested on a panel of four different parental MDR-1 expressing cell lines: the resistance index of L-Annamycin was significantly lower than that of doxorubicin, indicating that L-Annamycin is not cross-resistant with doxorubicin.

MDR-1 was identified as a major, independent negative prognostic factor in elderly patients with AML at diagnosis. In relapsed AML, a higher proportion of patients express MDR-1.

Anthracyclines are a class of antitumor agents. A particular class of anthracyclines are the 4-demethoxy-3'desamino-2'iodo analogs. This class is also described as compounds having the formula

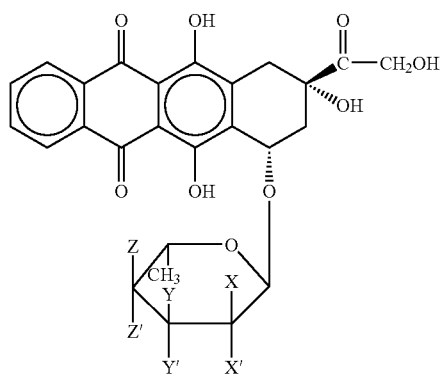

where one of X and X' is hydrogen and the other is halogen; one of Y and Y' is hydrogen and the other is selected from the group consisting of hydrogen, hydroxy, and —OCOR; one of Z and Z' is hydrogen and the other is selected from the group consisting of hydrogen, hydroxy, and —OCOR; where R is alkyl having approximately

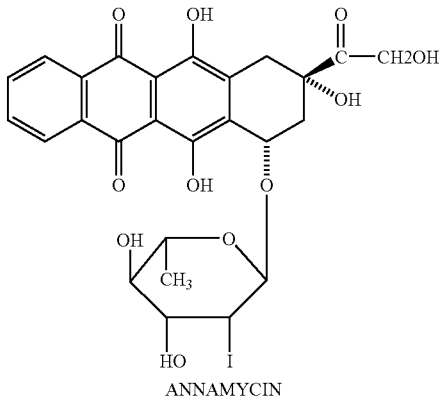

ANNAMYCIN

1–6 carbon atoms.

In liposomal forms, these compositions are encapsulated in a liposome, and particularly where the liposome comprises at least one lipid and a nonionic surfactant, and where the weight ratio of the anthracycline compound to the nonionic surfactant is between approximately 0.5:1 and approximately 3:1.

Particular reference is made to (7S,9S)-4-demethoxy-7-O-(2,6-dideoxy-2-iodo-alphamannopryanosyl) adriamycinone (4-DMD) or annamycin having the formula Annamycin is noteworthy as an anthracycline that is useful to overcome multidrug resistance (MDR), a response observed in many tumor cells. This is further illuminated in *Blood*, 88:633 (1996). In MDR, the tumor cell membrane glycoprotein, p-glycoprotein (p-gp), mediates resistance of doxorubicin, idarubicin, and mitoxantrone. Overexpression of p-gp is seen in a high percentage of patients with newly diagnosed refractory or relapsed leukemia.

SUMMARY OF THE INVENTION

This invention includes a method of treating a subject having relapsed or refractory cancer such as leukemia with liposomal annamycin by the steps of (a) evaluating the subject to determine if the subject has relapsed or refractory cancer;

(b) administering a high-dose amount of liposomal-annamycin for at least 3 days in a 7 day period. In some embodiments administration is for one or multiple consecutive days in a seven day period, with particular reference to 2, 3, 4, 5, 6 or 7 days. In some embodiments administration comprises a cycle of at least about 2 or more courses of administering a therapeutically effective amount of liposomal-annamycin for at least 2, or 3 or more days in a 7 day period, with a recovery period between courses. Periods of about 1, 2, 3 or more weeks are contemplated between courses. In some embodiments the high-dose amount of liposomal annamycin is at least about 280 mg/m$^2$, or at least about 350 mg/m$^2$, or at least about 500 mg/m$^2$ and up to about 1000 mg/m$^2$ or more. In some embodiments the method of claim further comprises administration of an adjunct antineoplastic drug such as all-trans retinoic acid, with particular reference to all-trans retinoic acid is in liposomal form. Note is made of adjunct treatment with all-trans retinoic acid administered at a dose of about 15 to 300 or more mg/m$^2$. Particularly noted is all-trans retinoic acid is administered at a dose of at least about 90 mg/m$^2$ in free or liposomal form.

This invention also comprises a method of treating a subject having cancer with particular reference to leukemia by the step of administering a high-dose amount of liposomal-annamycin for one or multiple consecutive days in a seven day period, with particular reference to 2, 3, 4, 5, 6 or 7 days. In some embodiments administration comprises a cycle of at least about 2 or more courses of administering a therapeutically effective amount of liposomal-annamycin for at least 2, or 3 or more days in a 7 day period, with a recovery period between courses. Periods of about 1, 2, 3 or more weeks are contemplated between courses. In some embodiments the high-dose amount of liposomal annamycin is at least about 280 mg/m$^2$ or at least about 350 mg/m$^2$, or at least about 500 mg/m$^2$ and up to about 1000 mg/m$^2$ or more.

In some embodiments the method of claim further comprises administration of an adjunct antineoplastic drug such as all-trans retinoic acid, with particular reference to all-trans retinoic acid is in liposomal form. Note is made of adjunct treatment with all-trans retinoic acid administered at a dose of about 15 to 300 or more mg/m$^2$. Particularly noted is all-trans retinoic acid is administered at a dose of at least about 90 mg/m$^2$ in free or liposomal form.

Neoplasms are also usefully treated by the methods of this invention.

DETAILED DESCRIPTION OF THE INVENTION

Figure 1:
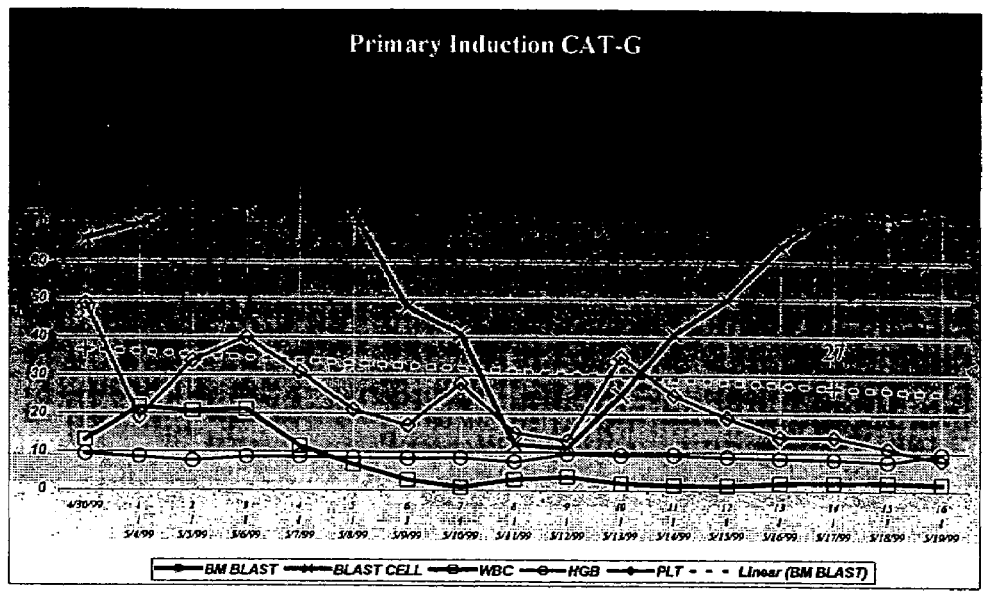
FIG. 1. is a graph of a subjects response to primary induction on CAT-G.

Liposomal annamycin has surprisingly been found to overcome cross-resistance to anthracycline drugs. Liposomal annamycin has been the subject of a clinical study of cancer patients with refractory or relapsed cancer. Particular reference is made to refractory or relapsed acute promyelocytic leukemia (AML).

This invention will be better understood with reference to the following definitions:

A. Relapsed and refractory are significant indications for liposomal annamycin cancer therapy.

Relapsed shall be understood to mean the presence of about ≧10% leukemic blast cells in blood or bone marrow in patients previously in complete remission.

Refractory shall be understood to mean the presence of about ≧5% of leukemic blast cells in blood or marrow of patients following chemotherapy, four weeks after initiation of such therapy, or persistence of leukemic blasts in blood or marrow 14 days after therapy started, with no evidence of decrease to <30%.

B. Evaluating as related to establishing whether or not a subject has relapsed or refractory cancer shall mean comparing a subjects presenting condition with the standards of relapsed and refractory as defined above. It is understood that clinical presentation is accompanied by a degree of variability, but the evaluation of subjects as relapsed or refractory is within the skill of an oncology medical. Particular note is made of patients with refractory or relapsed AML, myelodysplastic syndrom (MDS), refractory anemia with excess blasts (RAEB), refractory anemia with excess blasts in transformation (RAEB-T), chronic myelomonocytic leukemia (CMML), ALL or blast crisis of chronic myelogenous leukemia (CML) (lymphoid, myeloid and megakaryocytic).

C. High-dose liposomal annamycin shall mean at least about 250 mg/m$^2$, and further at least about 280 mg/m$^2$, or about 350 mg/m$^2$, and further at least about 500 mg/m$^2$, and further about 1 gm/m$^2$ or more. Reference to "m$^{2-}$" is to skin surface area in square meters. Calculated dosage is based on pure, anhydrous solvent free Annamycin.

Particular note is made of doses of 240 mg/m$^2$ which exhibited dose limiting thrombocytopenia accompanying treatment of solid tumors. In some instances, Grade IV plate counts were also noted, which was present in some instances even at doses of 210 mg/m$^2$.

It is understood that while high-dose annamycin is therapeutically effective as to liposomal anthracycline therapy in that slowing or stasis of cancer progression and, in some embodiments therapeutically effective dosing further includes regression and complete remission of cancer.

D. Complete remission shall mean normalization of the peripheral blood and bone marrow with 5% or less blasts, normocellular or hypercellular marrow, a granulocyte count of 1000 or above, and a platelet count of 100×10$^9$ /L or above. CR in both acute leukemia and CML-BP does not require disappearance of abnormal karyotype. In CML-BP, a return to chronic phase will be defined as CR, except for an elevation of WBC 10×10$^9$ /L or more with a CML differential.

E. Partial Remission shall mean the same as complete remission except for the presence of 6–25% blast. All other responses are considered failures.

F. A cycle as applied to therapy of the present invention shall mean administration of antineoplastic drug at least 3 times in a seven day period with at least about one week intervening between repeated doses. By way of example, administering a dosage of 280 mg/m$^2$ over about 1 to 2 hours each day for 3 consecutive days constitutes a course of administration and, and repeating the procedure 3 to 4 weeks later, and again 3 to 4 weeks later and then ceasing treatment for at least 8 weeks constitutes one treatment cycle.

Administration of liposomal annamycin by a variety or regimens is contemplated. In some embodiments, intravenous dosing is over a period of from about 30 minutes to about 4 hours, with particular reference to 1 to 2 hours. Dosing daily or every other day is anticipated with particular reference to dosing for 3 consecutive days with a hiatus between 3 day cycles. A hiatus or recovery period of from about 2 to about 6 weeks is noted with particular reference to about 3 to 4 weeks. In some embodiments recovery is characterized by a return of WBC, usually followed by rising platelet counts. In one embodiment, 3 dosage cycles are administered.

G. Leukemia is a condition which is usefully treated with L-annamycin. Particular reference is made to AML, myelodysplastic syndrom (MDS), refractory anemia with excess blasts (RAEB), refractory anemia with excess blasts in transformation (RAEB-T), chronic myelomonocytic leukemia (CMML), ALL or blast crisis of chronic myelogenous leukemia (CML) (lymphoid, myeloid and megakaryocytic), hairy cell leukemia.

Beyond resistant or refractory subjects, high-dose L-annamycin is a useful first line treatment. High-dose L-Annamycin treatment is usefully combined with other antineoplastic drugs.

MDR-1 mRNA Testing

In some embodiments, levels of MDT-1 mRNA were established by RT-PCR after the method of Drach D. et al., "Subpopulations of normal peripheral blood and bone marrow cells express a functional multidrug resistant phenotype," Blood 1:80(11):2729–34 (1992), the teachings of which are incorporated by reference. The multidrug-resistance gene, MDR1 is expressed in many normal tissues. Using the monoclonal antibody C219 and flow cytometric analysis, P-glycoprotein (P-gp) was found to be expressed in all peripheral blood (PB) subpopulations (CD4, CD8, CD14, CD1 9, CD56) except granulocytes. To specifically determine MDR1 gene expression, these PB subpopulations were isolated by fluorescence-activated cell sorting (FACS) and analyzed for MDR1 mRNA by-polymerase chain reaction (PCR). All subsets were positive by PCR, but only minimal MDR1 mRNA was detected in monocytes and granulocytes. Significant efflux of Rhodamine-123 (Rh-123), a measure of P-gp function, was detected in CD4+, CD8+, CD14+, CD19+, and CD56+cells but not in granulocytes. Next, PCR-analysis was performed on FACS-sorted bone marrow (BM) cells to assess MDR1 expression in different maturational stages. Precursors (CD34+), early and late myeloid cells (CD33+/CD34+, CD33+/CD34−) as well as lymphocytes of the B-cell lineage (CD19+/CD10+, CD19+/CD10−) expressed the MDR1 gene. BM monocytic cells (CD33++/CD34−) were negative, and a very weak signal was detected in erythroid cells (glycophorin A+). Significant Rh-123 efflux was found in CD34+, CD 10+, CD33+, and CD33++ BM cells, but not in glycophorin A+ cells. By this method expression of MDR1mRNA and a functional P-gp is determined in PB and BM lymphocytes, PB monocytes, BM progenitors, and immature myeloid cells. These results have to be taken into account when MDR1 expression is determined in tumor samples containing normal blood cells such that selection does not include MDR1 as contained in the normal cells. This method also was useful for testing of P-gp of CD34*blasts.

Liposomal-Annamycin

Liposomal Annamycin (2'-Iodo, 3'-hydroxy, 4'-epi, 4-demethoxy doxorubicin) was used in one embodiment of the present invention. Annamycin is a lipophilic anthracycline antibiotic that incorporates 4 structural modifications from doxorubicin: 2'-Iodo, 3'-hydroxy, 4'-epi, 4-demethoxy.

L-Annamycin is conveniently provided in the form of a preliposomal lyophilized powder containing a mixture of phospholipids, In one embodiment this is supplied as 20 mL vials containing 10 mg of Annamycin, or 100 mL vials containing 50 mg of Annamycin.

As a 50 mg vial one formulation is 50 mg Annamycin, dimysteroyl phosphatidyl choline (DMPC ) 1750 mg, dimyristoyl phosphatidyl glycerol (DMPG) 750 mg and Tween 20, 85 mg. "Tween™ " refers to a commercially available nonionic surfactant (ICI Americas Inc.) consisting of a mixture of different length chains of polyoxyethylene linked to a common sorbitan sugar. These polyoxyethylene sugars are also linked to a fatty acid. In the case of Tween™ 20, the composition is polyoxyethylene sorbitan monolaurate (MW approximately 1300).

As a 10 mg vial, one formulation is 10 mg Annamycin, DMPC 350 mg, DMPG 150 mg and Tween 20, 17 mg.

The lyophilate is conveniently reconstituted on the day of use. The drug is prepared by reconstituting the drug with saline (0.9% Sodium Chloride, Injection U.S.P.) at room temperature. It is useful to tap the vials prior to reconstitution to break up any dry cake. Reconstitute the 10 mg vial with 10 mL of saline, and the 50 mg vial with 50 mL of saline. Shake each vial back and forth for 2 minutes, or until suspended, to form liposomes (final Annamycin concentration approximately 1 mg/mL). If foaming occurs, allow vial to stand for a few minutes until foam subsides. Gently invert vial one more time to ensure against settling of the contents, and then transfer the reconstituted product to an empty IV bag for infusion. Take care to avoid transferring any foam.

EXAMPLE 1

A 57 year old white male with AML failed induction therapy of Cytoxan, Ara-C, Topotecan, and G-CSF (CAT-G).: After one course of CAT-G, bone marrow blasts decreased from 37% at baseline to 27% on Day 14. His circulating blasts remained high, having decreased from 66% at baseline to 11% on Day 9. From Day 9 his circulating blasts began to increase, and by Day 14 he had 74% circulating blasts. His response to CAT-G was declared a primary induction failure.

The relative levels of blood cell types arising from the CAT-G cycle is shown in FIG. 1. In both figured BM blast designates bone marrow blasts and is marked is with a box with an x. Blast cells are marked with an x. White blood cells are marked with a box. Platelets are marked with a diamond. Because bone marrow is not taken daily, the dotted line represents an average from points taken (percent blasts noted). Hemoglobin is shown in gm/deciliter. Cell counts are in thousands per microliter. Days are shown along the bottom of the graph.

Based on the history and clinical evaluation by MDT-1 mRNA and p-gp of CD34*blasts, the subject was determined to meet the criteria for refractory AML. The subject was moved to salvage on L-Annamycin.

Figure 2:
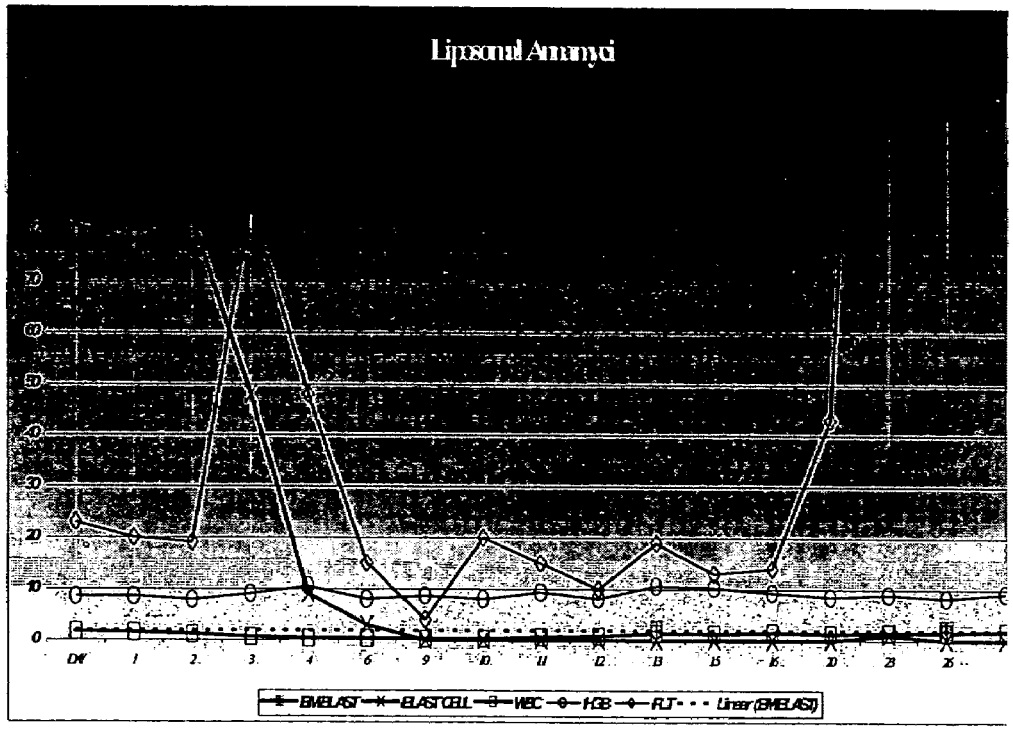
FIG. 2. is a graph of the same subjects response to L-annamycin.

The subject was administered the first course of liposomal annamycin at 280 mg/M$^2$ intravenously over one to two hours daily for three consecutive days. The relative levels of blood cell types is shown in FIG. 2.

The subject was further evaluated on days 8, 14, 21, and 28. By day 14, p-gp levels of CD34* were negative indicating preferential elimination of P-gp positive leukemic blasts. Two additional courses of treatment were administered identical to the initial course. Complete remission was established by normalization of peripheral blood and bone marrow with less than 5% blasts, normocellular or hypercellular marrow, a granulocytic count of count of 1000 or above, and a platelet count of 100×10$^9$ /L or above. Complete remission was ongoing at 2 months post-dosing. Relapse occurred after 13 weeks of complete remission.

The subject tolerated repeated courses of high-dose L-annamycin.

EXAMPLE 2

A 57 year old white male with AML is determined to meet the criteria for refractory AML.

The subject was administered the first course of liposomal annamycin at 360 mg/m$^2$ intravenously over one to two hours daily for three consecutive days.

The subject is further evaluated on days 8, 14, 21, and 28. By day 14, P-gp levels of CD34* is negative indicating preferential elimination of P-gp positive leukemic blasts. Two additional courses of treatment are administered identical to the initial course. Complete remission is established by normalization of peripheral blood and bone marrow with less than 5% blasts, normocellular or hypercellular marrow, a granulocytic count of count of 1000 or above, and a platelet count of 100×10$^9$ /L or above. Complete remission is ongoing at 2 months post-dosing.

The subject tolerated repeated courses of high-dose L-annamycin.

It will be appreciated that subjects treated with high dose L-annamycin are often in precarious condition and treatment is not without side effects and risk. It is within the skill of the medical professional to adjust dosage according to toleration and response. Subjects achieving a complete remission, after one or two courses of therapy usefully receive two additional consolidation courses of L-Annamycin at the previously best tolerated dose level until disease progression or lack of therapeutic benefit. In some regimens, therapy is repeated every 4–6 weeks if WBC is ≥3.0×10$^3$/μl, with an ANC ≥1.0×10$^3$/mL and platelets are ≥60×10$^3$/ml). Subjects who exhibit a favorable response of their leukemia, defined as a partial remission are usefully treated at the same dose level as the initial course, if Grade II or less non-hematologic toxicity has occurred. If they have a non-hematologic toxicity of Grade III or greater and a favorable response to therapy, another course of therapy is usefully administered.

Patients with an unfavorable response of their leukemia (stability or increase of blood or bone marrow blast), with Grade II or less non-hematologic toxicity (excluding nausea, vomiting, and alopecia), are usefully administered another course of chemotherapy at a higher dose level. At least 3 weeks should have elapsed since the prior course. As a guideline, such patients should have recovered from all toxicities. If the subject's blood counts have not recovered by day 35 (neutrophils ≧1×10$^9$/L and platelets ≧50×10$^9$/L) the patient is considered to have dose limiting hematological toxicity unless the decrease in blood cell count is secondary to persistent leukemia as documented by bone marrow aspiration studies or persistent peripheral blood blast.

The compositions of this invention possess valuable pharmacological properties. They inhibit the proliferation of neoplastic cells while avoiding MDR in cancer therapies.

Thus, these compositions can be used in cancers including blood cancers such as leukemia with particular reference to AML. Note is made of Hodgkin's disease, non-Hodgkin's lymphomas, acute and chronic lymphocytic leukemias, multiple myeloma, neuroblastoma, breast, ovary, and lung cancer, Wilms' tumor cervix, testis, and soft tissue sarcomas. Further noted is chronic granulocytic leukemia, malignant melanoma, choriocarcinoma, mycosis fungiodes, osteogenic sarcoma, hairy cell leukemia, Kaposi's sarcoma, essential thrombocytosis, prostate cancer and renal cancer.

Administration is contemplated to include chronic, acute or intermittent regimens. The compositions are particularly useful in the treatment of blood cancers such as AML.

In addition, the compositions can be used in in vitro methodologies, including extra corporeal treatment of blood and other tissue, as well as in diagnostics. In diagnostic embodiments cells are challenged in vitro with liposomal annamycin. In some embodiments, tissues, cells or material treated in vitro will, thereafter, be reintroduced into a subject (which need not be the source of origin of the tissue, cells or material). Compounds of the present invention are also useful in screening procedures. They can be employed in admixture or co-therapy with other drugs. Particular reference is made to such anti-cancer drugs as alkylating agents (nitrogen mustards, ethylenimines, alkyl sulfonates, nitrosoureas and triazines), antimetabolites (folic acid analogs, pytimidine analogs, and purine analogs), vinca alkaloids, epipodophylotoxins, antibiotics (actinomycin D, Bleomycin, plicamycin, doxorubicin, daunorubicin, and mitomycin C), enzymes such as I-asparginase Further note is made of biological response modifiers such as interferon-alpha, platinum coordination complexes such as cisplatin and carboplatin with specific reference to liposomal-ciplatin including diaminocyclohexane platinum complexes. Additionally noted are hormones and antagonists such as adrenocorticosteroids, is progestins, estrogens, antiestrogen, androgens, antiandrogen, and gonadotropin releasing hormone analog (leuprolide). Specific mention is made of retinoids such as all-trans retinoic acid (ATRA) and liposomal ATRA, as well as 13-cis retinoic acid. In some embodiments, all-trans retinoic acid is administered at a dose of about 15 to 300 or more mg/m$^2$, and particularly at least about 90 mg/m$^2$.

The compositions of this invention are generally administered to animals, including but not limited to humans.

The pharmacologically active compositions of this invention can be processed in accordance with conventional methods of Galenic pharmacy to produce medicinal agents for administration to patients, e.g., mammals including humans.

The compositions of this invention can be employed in admixture with conventional excipients, i.e., pharmaceutically acceptable organic or inorganic carrier substances suitable for parenteral, enteral (e.g., oral or inhalation) application which do not deleteriously react with the active compositions. Suitable pharmaceutically acceptable carriers include, but are not limited to water, and salt or sugar solutions, The pharmaceutical preparations can be sterilized and if desired mixed with auxiliary agents, e.g., preservatives, stabilizers, emulsifiers, salts for influencing osmotic pressure, buffers and the like which do not deleteriously react with the active compositions. They can also be combined where desired with other active agents as noted above.

In some embodiments of the present invention, dosage forms include instructions for the use of such compositions.

For parenteral application, particularly suitable are injectable, sterile solutions, preferably aqueous solutions, as well as suspensions. Ampules are convenient unit dosages.

Sustained or directed release compositions can be formulated, e.g., liposomes or those wherein the active component is protected with differentially degradable coatings, e.g., by microencapsulation, multiple coatings, etc. It is also possible to freeze-dry the new compositions and use the lyophilizates obtained, for example, for the preparation of products for injection.

Generally, the compositions of this invention are dispensed in unit dosage form comprising 10 to 800 mg in a pharmaceutically acceptable carrier per unit dosage.

The dosage of the compositions according to this invention generally are about 1.7 to 50 mg/kg/day, preferably about 2.5 to about 6mg/kg/day, when administered to patients, e.g., humans to treat leukemia.

It will be appreciated that the actual preferred amounts of active compositions in a specific case will vary according to the specific compositions being utilized, the particular compositions formulated, the mode of application, and the particular situs and organism being treated. Dosages for a given host can be determined using conventional considerations, e.g., by customary comparison of the differential activities of the subject compositions and of a known agent, e.g., by means of an appropriate, conventional pharmacological protocol. Note is made of the following:

1. DeVita V, Hellman S, Rosenberg S. (eds) *Principles and Practice of Oncology*, Ed. 4. Philadelphia: J.B. Lippincott Co., 1993.
2. Moscow J A, Cowan K H. Multidrug resistance. *J Natl Cancer Inst* 80:14–20, 1989.
3. Dalton W S. Multidrug resistance in DeVita V, Hellman S, Rosenberg S (eds), *Principles and Practice of Oncology*, Ed 4. Philadelphia: J.B. Lippincott Co., 1993.
4. Consoli U, Priebe W, Ling Y-H, Mahadevia R, Griffin M, Zhao S, Perez-Soler R, Andreeff M: The novel anthracycline annamycin is not affected by p-glycoprotein-related multidrug resistance: Comparison with idarubicin and doxorubicin in HL-60 leukemia cell lines. *Blood* 88(2):633–644, 1996.
5. Acton E M, Tong G L. Mosher C W, Wolgemuth R L. Intensely potent morpholinyl anthracyclines. *J Med Chem* 27:638–645, 1984.
6. Ganapathi R, Grabowski D, Sweatman T W, Seshadri R, Israel M. N-benzyladriamycin-14-valerate versus progressively doxorubicin-resistant murine tumors: cellular pharmacology and characterization of cross-resistance in vitro and in vivo. *Br J Cancer* 60:819–826, 1989.
7. Barbieri B, Giuliani F C, Bordoni T, Casazza A M, Geroni C, Bellini O, Suarato A, Gioia B, Penco S, Arcamone F. Chemical and biological characterization of 4'-iodo-4'deoxydoxorubicin. *Cancer Res* 47:4001–4006, 1987.
8. Priebe W, Van N T, Burke T G, Perez-Soler R. Removal of the basic center from doxorubicin partially overcomes multidrug resistance and decreases cardiotoxicity. *Anticancer Drugs* 4:37–48, 1993.
9. Gabizon A, Dagan A, Goren D, Barenholz Y, Fuks Z. Liposomes as in vivo carriers-of adriamycin: reduced cardiac uptake and preserved antitumor activity in mice. *Cancer Res* 42:4734–4739, 1982.
10. Rahman A, Carmichael D, Harris M, Roh J K. Comparative pharmacokinetics of free doxorubicin and doxorubicin entrapped in cardiolipin liposomes. *Cancer Res* 46:2295–2299, 1986.
11. Mayhew E, Rustum Y, and Vail W J. Inhibition of liver metastasises of M 5076 tumor by liposome-entrapped adriamycin. *Cancer Drug Delivery* 1:43–57, 1983.
12. Herman E H, Rahman A,. Ferrans V J, Vick J A, Schein P S. Prevention of chronic doxorubicin cardiotoxicity in beagles by liposomal encapsulation. *Cancer Res* 43:5427–5432, 1983.
13. Perez-Soler R, Priebe W. Anthracycline antibodies with high liposome entrapment: structural features and biological activity. *Cancer Res* 50:4260–4266, 1990.
14. Zou Y, Ling Y H, Van N T, Priebe W, and Perez-Soler R. Antitumor activity of free and liposome-entrapped Annamycin, a lipophilic anthracycline antibiotic with non-cross-resistance properties. *Cancer Res* 54-1479-1484, 1994.
15. Zou Y, Priebe W, Ling Y H, Perez-Soler R: Organ distribution and tumor uptake of Annamycin entrapped in multilamellar vesicles. *Cancer Chemother Pharmacol* 32:190–196, 1993.
16. Marie J P: Phenotypic and genotypic analyses of multidrug resistance (MDR) in clinical hospital practice. *Leukemia* 11:1063–1066, 1997.
17. Chaudhary P M, Roninson I B: Induction of multidrug resistance in human cells by transient exposure to different chemotherapeutic drugs. *J Natl Cancer Inst* 85:632–639, 1993.
18. Den Boer M L, Zwaan C M, Pieters R, Kazemier K M, Rottier M M A, Flens M J, Scheper R J, Veerman A J P:

Optimal immunocytochemical and flow cytometric detection of P-gp, MRP and LRP in childhood acute lymphoblastic leukemia. *Leukemia* 11:1078–1085, 1997.

19. Leith C, Chen I-M, Kopecky K, Appelbaum F. Head D, Godwin J, Weick J, Willman C: Correlation of multidrug resistance (MDR1) protein expression with functional dye/drug efflux in acute myeloid leukemia by multiparameter flow cytometry: Identification of discordant MDR-/efflux+ and MDR1 +/efflux- cases. *Blood* 86:2329–2342, 1995.

20. Zou Y, Hayman A, Priebe W, Perez-Soler R: Quantitative analysis of the lipophilic doxorubicin analog annamycin in plasma and tissue samples by reverse-phase chromatography. *J Pharm Sciences* 82:1151–1154, 1993.

All of the references cited herein are incorporated by reference.

We claim:

1. A method of treating a human subject having leukemia comprising the step of administering a dose of at least about 250 mg/m$^2$ of liposomal annamycin for at least 3 days in a 7 day period.

2. The method of claim 1 wherein said administration is for 3 consecutive days in a seven day period.

3. The method of claim 2 wherein said administration comprises a cycle of at least about 3 courses of administering a dose of at least about 250 mg/m$^2$ of liposomal-annamycin for at least 3 days in a 7 day period, with at least about 3 weeks between courses.

4. The method of claim 1 wherein said dose of liposomal annamycin is at least about 350 mg/m$^2$.

5. The method of claim 4 wherein said dose of liposomal annamycin is at least about 500 mg/m$^2$.

6. The method of claim 1 further comprising administration of an adjunct antineoplastic drug.

7. The method of claim 6 wherein said adjunct antineoplastic drug is all-trans retinoic acid.

8. The method of claim 7 wherein said all-trans retinoic acid is in liposomal form.

9. The method of claim 7 wherein said all-trans retinoic acid is administered at a dose of about 10 to 300 mg/m$^2$.

10. The method of claim 9 wherein said all-trans retinoic acid is administered at a dose of about 90 mg/m$^2$.

11. The method of claim 8 wherein said all-trans retinoic acid is administered at a dose of about 90 mg/m$^2$.

12. The method of claim 1, wherein the leukemia is acute myeloid leukemia (AML).

13. The method of claim 12, wherein the leukemia is refractory or relapsed leukemia.

14. The method of claim 1, wherein the leukemia is acute lymphoid leukemia (ALL).

15. The method of claim 1, wherein the leukemia is chronic myelomonocytic leukemia (CMML).

16. The method of claim 1, wherein the leukemia is chronic myclogenous leukemia.

17. The method of claim 16, wherein the leukemia is further defined as blast crisis of chronic myelogenous leukemia.

18. The method of claim 17, wherein blasts are lymphoid blasts, myeloid blasts, or megakaryocytic blasts.

19. The method of claim 1, wherein the leukemia is myelodysplastic syndrome.

20. The method of claim 1, wherein the leukemia is further defined as refractory anemia with excessive blasts.

21. The method of claim 20, wherein the leukemia is further defined as refractory anemia with excessive blasts in transformation.

22. The method of claim 1, wherein the leukemia is hairy cell leukemia.

* * * * *

UNITED STATES PATENT AND TRADEMARK OFFICE
CERTIFICATE OF CORRECTION

| | | |
|---|---|---|
| PATENT NO. | : 7,204,996 B2 | Page 1 of 1 |
| APPLICATION NO. | : 11/150461 | |
| DATED | : April 17, 2007 | |
| INVENTOR(S) | : Andreeff et al. | |

It is certified that error appears in the above-identified patent and that said Letters Patent is hereby corrected as shown below:

Title page, item [75], line 2, after "Elihu H" insert --.-- therefor.

In claim 16, column 12, line 18, delete "mycolgenous" and insert --myelogenous-- therefor.

Signed and Sealed this

Nineteenth Day of June, 2007

JON W. DUDAS
*Director of the United States Patent and Trademark Office*